United States Patent
Schatz et al.

[11] Patent Number: 6,027,509
[45] Date of Patent: Feb. 22, 2000

[54] STENT RETRIEVAL DEVICE

[75] Inventors: Richard A. Schatz, Rancho Santa Fe, Calif.; Brooke O. Ren, Champlin, Minn.

[73] Assignee: SciMed Life Systems, Inc., Maple Grove, Minn.

[21] Appl. No.: 08/942,432

[22] Filed: Oct. 1, 1997

Related U.S. Application Data

[60] Provisional application No. 60/028,054, Oct. 3, 1996.

[51] Int. Cl.[7] .................................................... A61F 11/00
[52] U.S. Cl. .............................................. 606/108; 604/96
[58] Field of Search ................................ 606/1, 108, 151, 606/157, 190–200; 623/1, 11, 12; 604/96–704

[56] References Cited

U.S. PATENT DOCUMENTS

| | | |
|---|---|---|
| 2,944,552 | 7/1960 | Cannon . |
| 3,421,509 | 1/1969 | Fiore . |
| 3,657,744 | 4/1972 | Ersek . |
| 3,842,441 | 10/1974 | Kaiser . |
| 3,993,078 | 11/1976 | Bergentz et al. . |
| 4,130,904 | 12/1978 | Whalen . |
| 4,140,126 | 2/1979 | Choudhury . |
| 4,313,231 | 2/1982 | Koyamada . |
| 4,315,509 | 2/1982 | Smit . |
| 4,434,797 | 3/1984 | Silander . |
| 4,483,339 | 11/1984 | Gillis . |
| 4,512,338 | 4/1985 | Balko et al. . |
| 4,562,596 | 1/1986 | Kornberg . |
| 4,594,996 | 6/1986 | Ibrahim et al. . |
| 4,732,152 | 3/1988 | Wallsten et al. . |
| 4,733,665 | 3/1988 | Palmaz . |
| 4,739,762 | 4/1988 | Palmaz . |
| 4,744,366 | 5/1988 | Jang . |
| 4,776,337 | 10/1988 | Palmaz . |
| 4,793,348 | 12/1988 | Palmaz . |
| 4,800,882 | 1/1989 | Gianturco . |
| 4,886,062 | 12/1989 | Wiktor . |
| 4,907,336 | 3/1990 | Gianturco . |
| 4,913,141 | 4/1990 | Hillstead ................................ 606/108 |
| 4,921,478 | 5/1990 | Solano et al. ............................. 604/53 |
| 4,932,959 | 6/1990 | Horzewski et al. ..................... 606/194 |
| 5,026,377 | 6/1991 | Burton et al. ........................... 606/108 |
| 5,053,013 | 10/1991 | Ensiminger et al. ................... 604/167 |
| 5,156,596 | 10/1992 | Balbierz et al. ........................ 604/164 |
| 5,275,605 | 1/1994 | Winkler .................................. 606/128 |
| 5,330,482 | 7/1994 | Gibbs et al. ............................ 606/113 |
| 5,334,208 | 8/1994 | Soehendra et al. ..................... 606/108 |
| 5,388,590 | 2/1995 | Horrigan et al. . |
| 5,409,495 | 4/1995 | Osborn .................................. 606/108 |
| 5,411,507 | 5/1995 | Heckele ................................. 606/108 |
| 5,474,563 | 12/1995 | Myler et al. ............................ 606/108 |
| 5,520,697 | 5/1996 | Lindenberg et al. ................... 606/108 |
| 5,628,754 | 5/1997 | Shevlin et al. ......................... 606/108 |
| 5,634,937 | 6/1997 | Mollenauer et al. ................... 606/213 |
| 5,830,218 | 11/1998 | Ren et al. .............................. 606/108 |

FOREIGN PATENT DOCUMENTS

| 0 274 846 | 7/1988 | European Pat. Off. . |
|---|---|---|
| 2 104 673 | 5/1972 | Germany . |

*Primary Examiner*—Glenn K. Dawson
*Attorney, Agent, or Firm*—Crompton, Seager & Tufte, LLC

[57] ABSTRACT

A device and method for retrieving balloon expandable stents. The device can be used with a guide catheter having a balloon angioplasty catheter inserted within. The invention includes a grasping device at the distal end of a shaft and a means for closing the grasping device. In one embodiment, the grasping device includes a reinforced tube having a bound inner sleeve, two inflatable inner balloons and a longitudinal slit. In use, the tube can be slipped over the proximal portion of a balloon catheter shaft extending from a patient, compressed to reduce the profile, advanced over the shaft, through and distally out of a guide catheter, allowed to recover the original profile, advanced over a stent, inflated to grasp the stent distal end within, and retracted proximally into the guide catheter.

8 Claims, 2 Drawing Sheets

STENT RETRIEVAL DEVICE

RELATED CASE

This application claims the benefit of U.S. Provisional application Ser. No. 60/028,054, filed Oct. 3, 1996.

FIELD OF INVENTION

The present invention relates generally to a method and device for stent retrieval.

Background of the Invention Stents are increasingly used in Percutaneous Transluminal Coronary Angioplasty (PTCA). PTCA is a well established procedure for dilating stenosed vessel regions in the heart. In this procedure, a balloon angioplasty catheter is introduced into the vasculature, typically though an incision in the femoral artery in the groin. The balloon catheter is advanced through the femoral artery, through the aortic arch, and into the artery to be treated. The balloon is advanced across a lesion and inflated, dilating the vessel at the location of the balloon expansion. The dilation increases the vessel cross sectional area and the resultant blood flow.

Over a period of time, the dilated vessel section may narrow again, in part due to a rebound from the angioplasty procedure, thereby reversing some of the benefits of the angioplasty. To prevent this vessel narrowing, stents are increasingly used. Stents are placed across the dilated region and radially expanded, opposing any inward radial force by the vessel walls.

Stents may be categorized as self-expanding and balloon expanding. The self-expanding stents are contained within a sheath to prevent premature expansion. The stent is placed within a guide catheter, moved across a lesion, withdrawn from the sheath, and the stent, being biased to expand, expands, ideally with sufficient force to resist the vessel wall rebound force which can occur after angioplasty. The stent can be left in place indefinitely.

Balloon-expandable stent deployment requires "tacking up" the stent, forcing stent struts or members radially outward into close proximity with the vessel wall. The stent is mounted over an uninflated balloon, crimped, and the balloon with stent advanced within a guide catheter. The balloon with stent is advanced distally out of the guide catheter across the lesion. The balloon is inflated, expanding the stent, thereby tacking the stent in place. For optimal stent placement, it is necessary for the stent to be properly positioned axially on the balloon prior to balloon inflation. A non-compliant balloon operated at high pressure is typically used to expand the inside diameter of the stent, forcing it against the vessel interior walls. The balloon is deflated, and withdrawn proximally into the guide catheter.

For both types of stents, self-expanding and balloon expandable, a sheath can be used during stent delivery, being interposed between stent and guide catheter. The sheath adds a not-insubstantial thickness around the stent, increasing the vessel inside diameter required to pass the sheathed stent. In one case, when using a sheath, a sheath outside diameter of 72 mils (thousands of an inch) is required to place a stent having an outside diameter of 60 mils. When not using a sheath, clearance is only required for the 60 mil sheath. This reduced outer diameter translates into increased vasculature accessible for stent placement, making treatable otherwise untreatable lesions.

As a result of the increased vasculature reachable without sheaths, treating physicians increasingly prefer to place stents without using a sheath, the "bare mounted" technique. This is possible with balloon-expanding stents, but has associated difficulties. A stent can be bare mounted over a balloon, crimped, and the balloon advanced through the guide catheter to the distal region of the guide catheter, which is positioned proximal to the vessel region having a lesion. The balloon with stent is advanced distally out of the guide catheter and across the lesion. When the stent is crimped onto the balloon, there can be a slight recoil, such that when balloon and stent are advanced out of the guide catheter, the stent is too large to be retracted into the guide catheter even before balloon inflation.

Occasionally, there are situations where the stent becomes partially or totally dislodged from the balloon. The dislodged stent may be detected while still within the guide catheter. A dislodged stent can be detected using radiography, observing relative positions of radiopaque regions on the stent and balloon catheter. When the stent is dislodged while within the guide catheter, it may be possible to withdraw the balloon catheter and stent together.

At other times, the stent becomes dislodged after the stent has been advanced out of the guide catheter. As the balloon-expanding stents do not self-expand, this creates the situation where a stent may become loose in the vasculature. When the stent is only partially dislodged from the balloon, the balloon with partially mounted stent may be withdrawn proximally into the guide catheter. The stent outer diameter is often only slightly less than the inner diameter of the guide catheter, to keep the guide catheter size down and increase the amount of vasculature open to the guide catheter. The stent outer diameter may be larger than the guide catheter inner diameter, and withdrawal of the balloon will not withdraw the stent, but may instead force the stent off the balloon.

In cases where the stent remains sufficiently small to fit within the guide catheter, withdrawal may still prove problematic. During attempted recovery, there is a point at which the proximal edge of the stent is to be withdrawn proximally past the distal edge of the guide catheter. If the stent is not centered relative to the longitudinal axis of the guide catheter, the guide catheter distal edge may catch against the stent proximal edge, forcing the stent from the balloon.

What would be desirable is a device for retrieving a partially deployed stent. A device for grasping, compressing, and retracting a stent has not hereto been provided.

SUMMARY OF THE INVENTION

The present invention provides a device and method for retrieving stents from within a body conduit such as a vein or artery. While the preferred use of the invention is to retrieve coronary stents, use in retrieving stents from other body conduits is contemplated and is explicitly within the scope of the invention.

This can be accomplished by side mounting a stent retriever tube having inner inflatable balloons over the proximal end of a balloon catheter shaft, compressing the tube thereby decreasing the profile, advancing the tube through the guide catheter to the stent, allowing the tube to recover its full profile, pulling a slight vacuum on the inner balloons, advancing the tube over the stent, inflating the inner balloons, grasping the stent, and withdrawing the stent into the guide catheter. While the preferred embodiment mounts over a balloon catheter shaft, the invention may be mounted over other shafts, including guide wires, and may be used without any shaft at all. The preferred embodiment is advanced within a guide catheter, but advancement within other elongate tubes is contemplated and is also within the scope of the invention.

In one embodiment, the retrieval device includes an elongate shaft having a longitudinally slit tube mounted at the distal end. The preferred tube includes a metal (e.g., stainless steel, super-elastic alloy) spine and rib cage having a polymeric sheath bonded to the interior, exclusive of the slit. The tube further includes at least one inflatable inner balloon, attached near the interior wall of the tube. The preferred embodiment has two or more inflatable balloons. The shaft preferably includes hypotube in fluid communication with the inflatable balloons. While tubular shaped balloons are preferred, running substantially the length of the tube, other sized balloons, including a concentric, double walled, inflatable sleeve, is contemplated for use as the balloon. The transition from tube to shaft includes a shoulder, preferably formed of polymeric material. When inflation fluid is supplied to the inflatable balloons, the balloons increase in diameter, decreasing the effective inside diameter of the tube, grasping and compressing any stent within the tube, enabling the capture and withdrawal of a stent.

In use, the slit tube is mounted over a shaft lying within a guide catheter, such as a stent placement balloon shaft. The tube is compressed by curling one side of ribs inside the other side of ribs near the tube slit. The tube is advanced through the guide catheter, exiting the guide catheter distally, and allowed to recover its original profile. The tube is advanced over the stent, and inflation fluid is supplied to inner balloons, decreasing the effective inside diameter, grasping and compressing the stent. The tube grasping the stent is then withdrawn into and through the guide catheter and out of the patient.

DETAILED DESCRIPTION OF THE PREFERRED EMBODIMENTS

Figure 1:
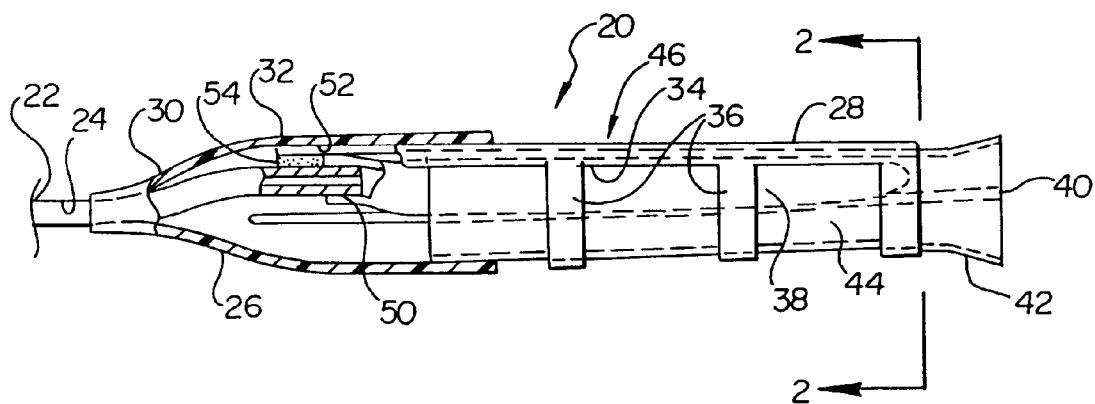
FIG. 1 illustrates a fragmentary side view of a slit tube grasping device having inflatable inner balloons.

FIG. 1 illustrates a stent retrieval device 20 embodying the present invention including a tube portion 46 and a shaft portion 22, tube 46 being attached to a distal region of shaft 22, and having a proximal shoulder 30 decreasing in diameter from tube 46 to shaft 22. A preferred embodiment includes a longitudinal slit 40 running the entire length of tube 46 and through shoulder 30 for side mounting tube 46 over a shaft. Tube 46 can be mounted over the proximal region of a balloon catheter shaft extending proximally from a guide catheter within the patient. In a preferred embodiment, tube 46 includes radial reinforcing ribs 36 joined to a longitudinal spine 34. In a preferred embodiment, there are three ribs.

In one embodiment, tube 46 has a slight taper over its length, having a larger inside diameter distally then proximally. This aids in stent withdrawal by presenting a smaller profile to the guide catheter distal end upon withdrawal while presenting a larger inside diameter to the stent to be captured.

A preferred method of making ribs 36 and spine 34 is to laser cut a piece of NITINOL tubing, for example, 0.063 inch outside diameter tubing having 0.004 inch wall thickness. The laser cutting leaves spine 34 and ribs 36 as a single piece.

Shaft 22 can be fixedly attached to spine 34 at spine stem 52 by soldering, as indicated at 54. In a preferred embodiment, shaft 22 is formed of stainless steel hypotube which includes inflation lumen 24.

A preferred embodiment of tube 46 has a tube interior sheath 44 forming the inner wall of tube 46. Sheath 44 substantially covers the inside of tube 46 including ribs 36 and spine 34, but not covering slit 40. In a preferred embodiment, sheath 44 is formed by bonding angioplasty balloon material within the interior of tube 46, leaving slit 40 open. The most preferred sheath material is polyolefin or fluoropolymer. The most preferred method of bonding sleeve to ribs utilizes adhesive.

One embodiment has a single inner balloon within tube 46. The most preferred embodiment has two inner balloons 38, within tube 46. In the most preferred embodiment, balloon 38 is bonded along a side to the interior of sheath 44, holding balloon 38 away from tube center. Balloon 38 is in fluid communication with inflation lumen 24.

The preferred embodiment includes a shoulder collar 32 over shoulder 30, providing a transition from tube 46 to shaft 22. In one embodiment, shoulder 30 is conical shaped. In a most preferred embodiment, shoulder 30 has a contour as illustrated in FIG. 1. In a preferred embodiment, shoulder collar 32 is formed from polyolefin or fluoropolymer. Shoulder collar 32 can be formed by wrapping a piece of polymeric material over shoulder 30 and bonding it in place using adhesive.

A preferred embodiment includes a distal receiver 42 attached to the distal region of tube 46. Distal receiver is preferably tapered, having a larger inside diameter at the distalmost end than at the proximalmost end. In the preferred embodiment, distal receiver 42 is flares as illustrated in FIG. 1. Distal receiver 42 can be made from the same material as inner sheath 44, and may be formed in one piece with inner sheath 44. Distal receiver 42 serves to guide and center a stent relative to tube 46 center during stent capture.

Figure 2:
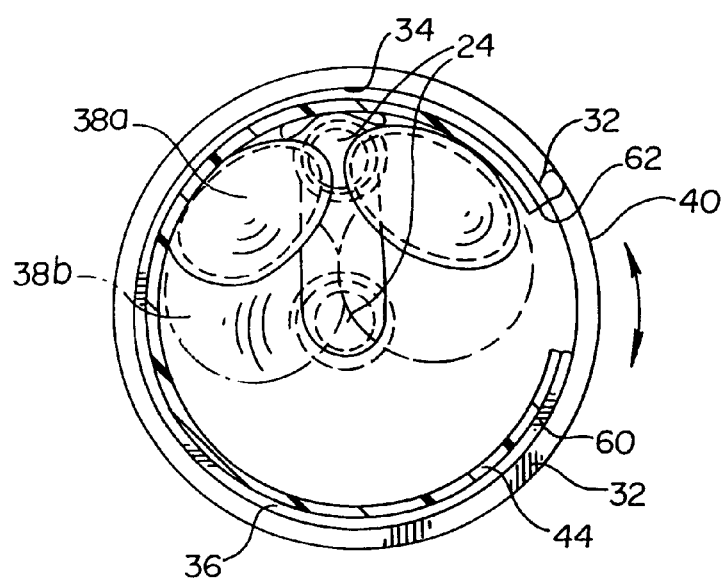
FIG. 2 is a cross-section projection view of the device of FIG. 1, taken along 2—2.

FIG. 2 illustrates a cross section taken through the distal portion of tube 46 distal to the distalmost rib 36. Ribs 36 are shown divided into long rib 60 and short rib 62 by slit 40. In a preferred embodiment, slit 40 is not located directly opposite spine 34. In a most preferred embodiment, slit 40 is located 90 degrees relative to spine 34. Sheath 44 is interior to ribs 36 in the preferred embodiment. Shoulder collar 32 is shown in background in FIG. 2.

Balloons 38 are shown in both deflated state 38a and inflated state 38b in FIG. 2. When tube 46 is advanced toward the stent, balloons 38 are deflated, preferably under a small vacuum. When tube 46 has advanced over the stent to be captured, balloons 38 are pressurized, decreasing the effective inside diameter of the tube, thereby grasping and compressing the captured end of the stent.

In use, when a balloon catheter is positioned in the patient within a guide catheter, having a stent near the balloon, the distal region of a stent retrieval device is side mounted over a proximal region of the catheter shaft laying outside the patient, and compressed to fit within the guide catheter if necessary. The grasping device portion of the retrieval device is advanced into the patient, distally out of the guide catheter, to the stent. The stent is then grasped by inflating the inner balloons, and pulled back into the guide catheter and withdrawn from the patient.

FIGS. 3–6 illustrate the problem and its solution by the present invention. The embodiment of FIG. 1 is shown for example, in highly diagrammatic form.

Figure 3:
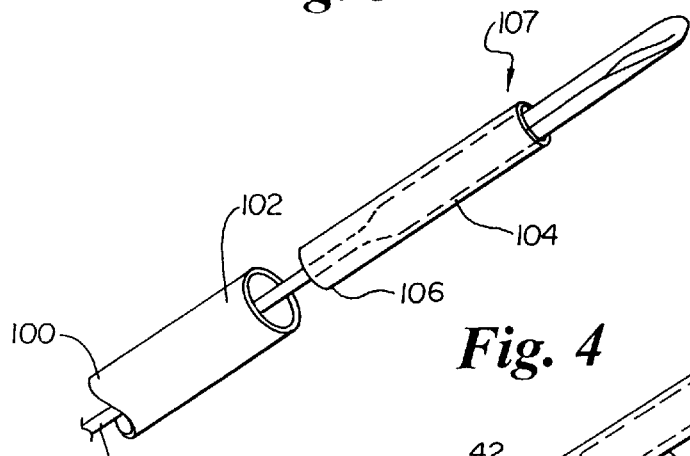
FIG. 3 illustrates a highly diagrammatic, perspective view of a partially deployed stent, balloon catheter, and guide catheter.

FIG. 3 illustrates a guide catheter 100, including a distal end 102, having an inflatable balloon catheter 107 inserted therethrough, including a catheter shaft 110, and balloon 108. Stent 104 is shown, having slipped proximally from the desired, mid-balloon position. Distal slippage presents a similar problem. Stent 104 includes a proximal end 106. As shown, withdrawing balloon catheter 107 into guide catheter 100 presents the possibility of guide catheter distal end 102 pushing stent 104 distally off balloon 108. Even in situations where stent 104 has an outer diameter small enough to fit within guide catheter 100, the possibility of guide catheter 100 dislodging stent 104 upon catheter withdrawal remains. This possibility exists if device catheter shaft 22 is not sufficiently centered within guide catheter 100, thereby allowing stent to be withdrawn proximally while off-center. Such an off-center withdrawal can allow stent 104 to be pushed distally by part of guide catheter distal end 102.

In the preferred method of stent retrieval, tube 46 is side mounted over catheter shaft 110 using slit 40, and is reduced in cross sectional area by compressing ribs 36, forcing ribs on one side of slit 40 radially inward, curling tube 46, causing short ribs 62 and long ribs 60 to overlap one another near slit 40. Tube 46 is thereby curled around shaft 110. Tube 46 is advanced distally over the balloon catheter shaft by advancing device shaft 22, through the guide catheter, exiting the guide catheter distal end. Upon exiting the guide catheter, tube 46 is free to expand its original, larger, inside diameter. In a preferred embodiment, ribs 36 are made of NITINOL, which allows tube 46 to return to its original diameter when warmed to body temperature.

Figure 4:
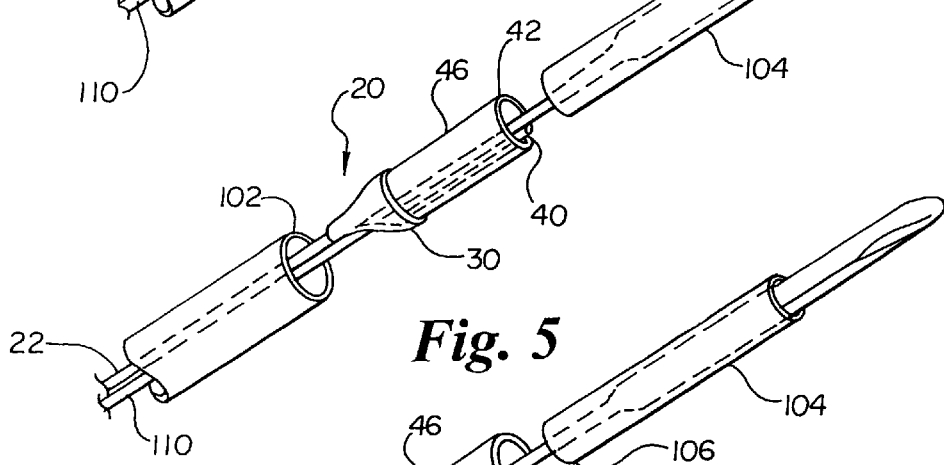
FIG. 4 further illustrates the perspective view of FIG. 3, including the stent retrieval device of FIG. 1 before stent capture and before tube profile recovery.
Figure 5:
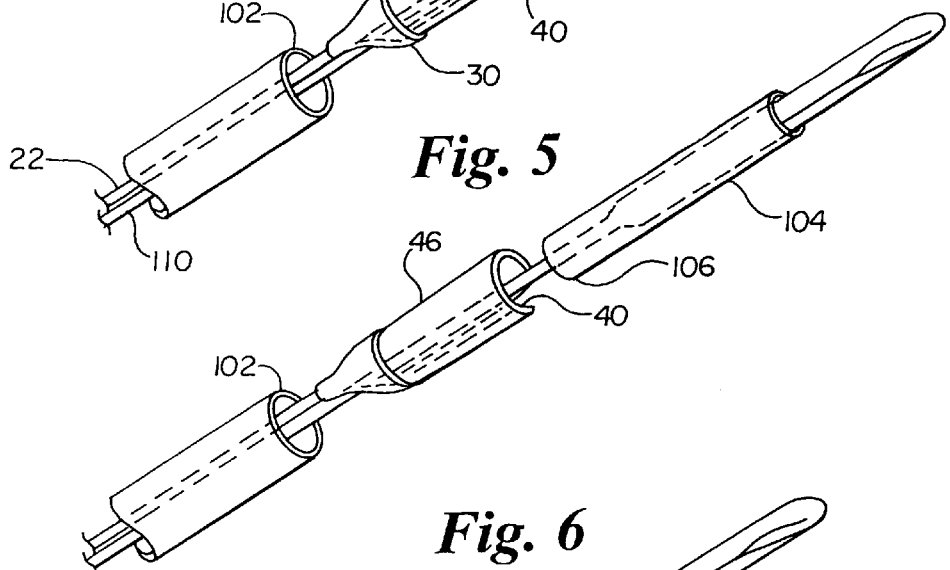
FIG. 5 further illustrates the perspective view of FIG. 3, including the stent retrieval device of FIG. 1 before stent capture after profile recovery.

FIG. 4 illustrates the stent retrieval device embodiment of FIG. 1, distal of guide catheter distal end 102. The device is shown prior to full profile recovery. FIG. 5 illustrates the stent retrieval device embodiment of FIG. 1, distal of guide catheter distal end 102. The device is shown, having recovered the full profile present prior to insertion into the guide catheter. As illustrated in FIG. 5, the device distal region is sufficiently large enough to contain stent proximal end 106.

Figure 6:
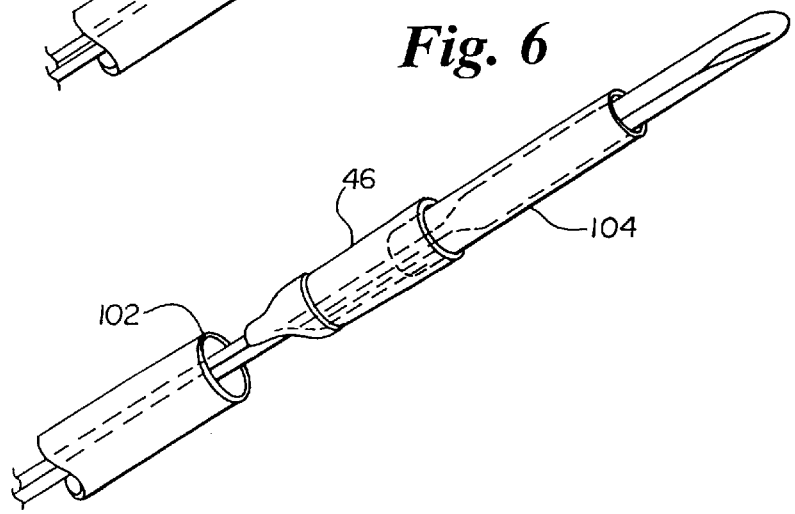
FIG. 6 further illustrates the perspective view of FIG. 3, including the stent retrieval device of FIG. 1 after stent capture.

With the aid of radiographic visualization, tube 46 is advanced until tube distal receiver 42 surrounds stent proximal end 106. In the preferred method, a slight vacuum is pulled on balloons 38 to increase the effective inside diameter of tube 46. Tube 46 is further advanced, with distal receiver 42 guiding stent 104 into the center axis of the tube. With the stent at least partially within tube 46, inflation fluid pressure is applied, inflated balloons 38 to position 38b as illustrated in FIG. 2. The increased balloon profile decreases the effective inside diameter available to the stent, thereby grabbing and compressing the stent With the stent firmly grasped as illustrated in FIG. 6, tube 46 is withdrawn proximally toward the guide catheter distal end. Shoulder 30 is drawn first into the guide catheter, centering tube 46 within the guide catheter and presenting a smooth contour for withdrawal. As device shaft 22 is stronger in tension than compression, a larger profile for tube 46 and a larger amount of friction is more tolerable during device withdrawal than device advancement. Tube 46 is further withdrawn, exiting the patient's body and the guide catheter.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A stent retrieval device comprising:
    an elongate shaft having an inflation lumen and a distal region;
    a tube, said tube operatively attached to said shaft distal region, wherein said tube includes a proximal shoulder extending proximally from said tube proximal region to said shaft, decreasing proximally in outer diameter and wherein said tube includes a longitudinal slit; and
    an inflatable balloon within said tube, said balloon being in fluid communication with said shaft inflation lumen.

2. A stent retrieval device as recited in claim 1, wherein said slit is substantially linear.

3. A stent retrieval device as recited in claim 2, wherein said tube includes a plurality of reinforcing ribs.

4. A stent retrieval device as recited in claim 3, wherein said tube includes a distal region, said device further comprising
    a distal receiver, said receiver operatively attached to said tube distal region and tapered, having a distalmost inside diameter greater than a proximalmost inside diameter.

5. A method for retrieving a stent comprising:
    providing a stent retrieval device including an elongate shaft having a distal region, a retrieval tube operatively attached to said shaft distal region, said retrieval tube having at least one inflatable balloon attached within said tube interior, said retrieval tube decreasing in effective inside diameter when said balloon is inflated;
    inserting an elongate tube intravascularly into a patient, a portion of said elongate tube extending proximally therefrom, a stent being positioned near the distal end of said elongate tube;
    advancing said retrieval tube distally into said patient;
    advancing said retrieval tube distal end toward said elongate tube distal end;
    advancing said retrieval tube distal end until a portion of said stent proximal end is within said retrieval tube distal end,
    decreasing said retrieval tube effective inside diameter;
    retracting said retrieval tube containing said stent proximally.

6. A method as recited in claim 5, wherein said elongate tube is a guide catheter.

7. A method as recited in claim 6, wherein said guide catheter has a balloon catheter inserted therethrough, further comprising selecting a section of balloon catheter shaft proximal to said patient's body and moving said retrieval tube over said catheter shaft.

8. A method as recited in claim 7, wherein said retrieval tube has a longitudinal slit therethrough, further comprising selecting a section of balloon catheter shaft proximal to said patient's body and moving said retrieval tube slit over said catheter shaft.

* * * * *